United States Patent [19]
Gaddis

[11] Patent Number: 5,748,657
[45] Date of Patent: May 5, 1998

[54] HIGH EFFICIENCY CONSTANT CURRENT LASER DRIVER

[75] Inventor: Mark W. Gaddis, Albuquerque, N. Mex.

[73] Assignee: The United States of America as represented by the Secretary of the Air Force, Washington, D.C.

[21] Appl. No.: 716,663

[22] Filed: Aug. 26, 1996

[51] Int. Cl.⁶ ............................... H01S 3/00; A61B 17/36
[52] U.S. Cl. ................... 372/38; 372/109; 372/43; 606/10; 606/11
[58] Field of Search ................... 372/33, 25, 38, 372/43, 46, 30, 109; 606/1, 2, 10, 11, 12

[56] References Cited

U.S. PATENT DOCUMENTS

| | | |
|---|---|---|
| 4,535,458 | 8/1985 | Inoue et al. .................... 372/25 |
| 4,751,524 | 6/1988 | Balchunas .................... 346/108 |
| 4,827,116 | 5/1989 | Takagi et al. .................... 372/38 X |
| 4,921,357 | 5/1990 | Karube et al. .................... 372/38 |
| 5,309,461 | 5/1994 | Call et al. .................... 372/38 |
| 5,319,190 | 6/1994 | Allen et al. .................... 250/214 |
| 5,377,213 | 12/1994 | Honda .................... 372/38 |
| 5,473,623 | 12/1995 | Fahey et al. .................... 372/38 |
| 5,477,557 | 12/1995 | Inaba et al. .................... 372/38 |
| 5,500,867 | 3/1996 | Krasulick .................... 372/38 |
| 5,661,745 | 8/1997 | Kim et al. .................... 372/70 |

*Primary Examiner*—Brian Healy
*Attorney, Agent, or Firm*—William G. Auton

[57] ABSTRACT

A constant current laser driver circuit that will drive a laser diode in a constant current mode from a 6 to 12 volt battery supply. The laser driver consists of two main sections. The first section converts the 12 volt input to a 2 volt output using ultra-low resistance power mosfets and an inductor. The current sensing amplifier senses the current flowing through the laser and sends a feedback signal to the switching section, which causes it to adjust the output voltage to keep the laser driving current constant.

4 Claims, 2 Drawing Sheets

HIGH EFFICIENCY CONSTANT CURRENT LASER DRIVER

STATEMENT OF GOVERNMENT INTEREST

The invention described herein may be manufactured and used by or for the Government for governmental purposes without the payment of any royalty thereon.

BACKGROUND OF THE INVENTION

This invention relates generally to laser power supplies, and more specifically the invention pertains to a laser driver circuit to drive high power lasers (1 watt–20 watts) with a constant current and with high efficiency.

The present invention was designed for use with a portable field medical system, of U.S. patent application Ser. No. 08/385,002, the disclosure of which are incorporated herein by reference.

The field medical system includes a portable, battery-operated surgical laser system that is intended to cut like a scalpel and coagulate bleeding. The laser system described above require a high power constant current laser power supply.

Prior art constant current power supply systems are described in the following U.S. Patents, the disclosures of which are incorporated herein by reference:

U.S. Pat. No. 4,751,524 issued to Balchunas;

U.S. Pat. No. 5,309,461 issued to Call et al; and

U.S. Pat. No. 5,477,557 issued to Inaba.

While the above-cited patents are instructive they refer to low-power laser driver systems. A need remains for a high-power, constant current laser driver power supply. The present invention is intended to satisfy that need.

SUMMARY OF THE INVENTION

The present invention is a constant current laser driver circuit that will drive a laser diode in a constant current mode from a 6 to 12 volt battery supply. The laser driver consists of two main sections. The first section converts the 12 volt input to a 2 volt output using ultra-low resistance power mosfets and an inductor. The current sensing amplifier senses the current flowing through the laser and sends a feedback signal to the switching section, which causes it to adjust the output voltage to keep the laser driving current constant. To reduce the input voltage to the 2 volts needed by the laser diode normally requires resistors, transistors or voltage regulators which can waste up to 85% of the input power in the form of heat. The switching regulator can supply a constant current with the required voltage to drive a laser diode, at efficiencies greater than 85%. Very little input power is wasted as heat.

One embodiment of the invention was designed for use with the portable field medical system of the above-cited patent application, which uses the laser as a scalpel to both cut and cauterize tissues. This surgical laser presents a variable load for the power supply, and a constant current with high efficiency is a challenge.

The medpack laser driver uses the latest DC to DC converter technology combined with extremely low resistance power mosfets to provide a compact, highly efficient package which is ideally suited for battery powered field devices. Typical efficiency is greater than 82% for load currents up to 30 amps. This helps to reduce energy losses due to heat generation in the laser driver, and also increases life of the power source battery.

An important requirement for laser driver circuits is that they accurately regulate the current flowing through the laser. The current variation for this device is typically less than 1% as the input is varied between 9 and 15 volts. Current overshoot at turn-on is less than 0.5%.

DC to DC converter technology helps to reduce the current drain on the battery power source. The supply current is reduced by approximately the ratio of Vin/Vout. In the present application, which uses a 12 volt battery, the battery has to supply 3.5 amps for a laser load of 20 amps at 2 volts. This is a 6 times improvement over a circuit using a voltage regulator to reduce the input voltage.

The medpack laser driver also has a unique feature which allows it to utilize nearly 100% of the available battery energy. The internal low-dropout current regulator will keep the laser current constant until the battery voltage drops below 3.8 volts. This will give a longer useful run-time per battery charge.

It is an object of the present invention to provide a constant current power supply to a portable laser system using a direct current battery as a voltage source.

It is another object of the invention to provide a direct current power supply for a laser that has high efficiency to conserve battery power.

These objects together with other objects, features and advantages of the invention will become more readily apparent from the following detailed description when taken in conjunction with the accompanying drawings wherein like elements are given like reference numerals throughout.

DETAILED DESCRIPTION OF THE PREFERRED EMBODIMENTS

The constant current laser driver of the present invention was developed to efficiently drive a laser diode in constant current mode from a 6–12 volt battery supply. To reduce the input voltage to the 2 volts needed by the laser diode normally required resistors, transistors or voltage regulators which can waste up to 85% of the input power in the form of heat. The switching regulator can supply a constant current with the required voltage to drive a laser diode, at efficiencies greater than 85%. Very little input power is wasted as heat.

Figure 1:
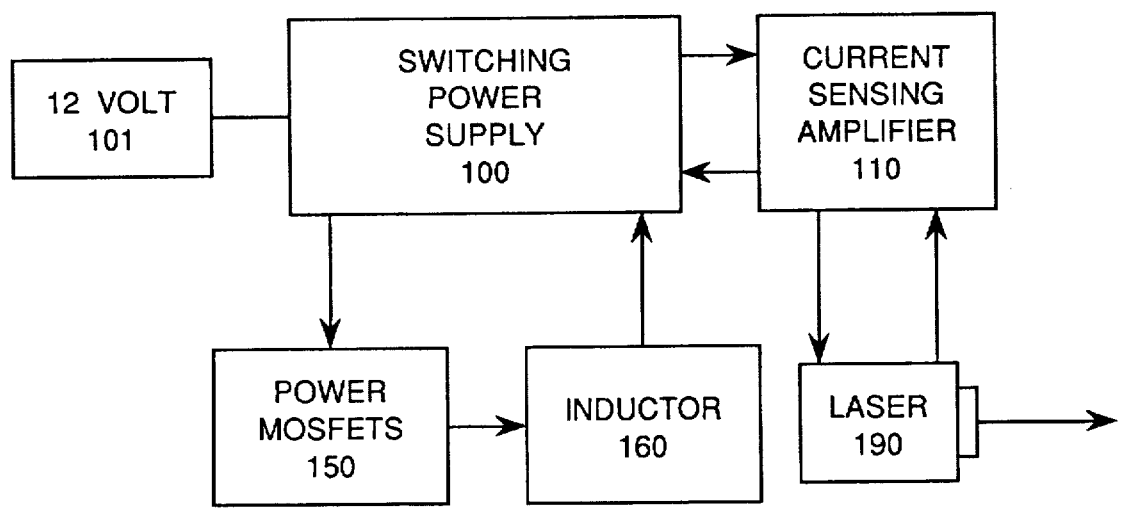
FIG. 1 is a block diagram of the present invention.

The reader's attention is now directed towards FIG. 1, which is a block diagram of the laser driver of the present invention.

The laser driver consists of two main sections. The first section converts the 12 volt input 101 to a 2 volt output using ultra-low resistance power mosfets 150 and an inductor 160. The current sensing amplifier 110 senses the current flowing through the laser 190 and sends a feedback signal to the switching section 100 which causes it to adjust the output voltage to keep the laser driving current constant.

Figure 2:
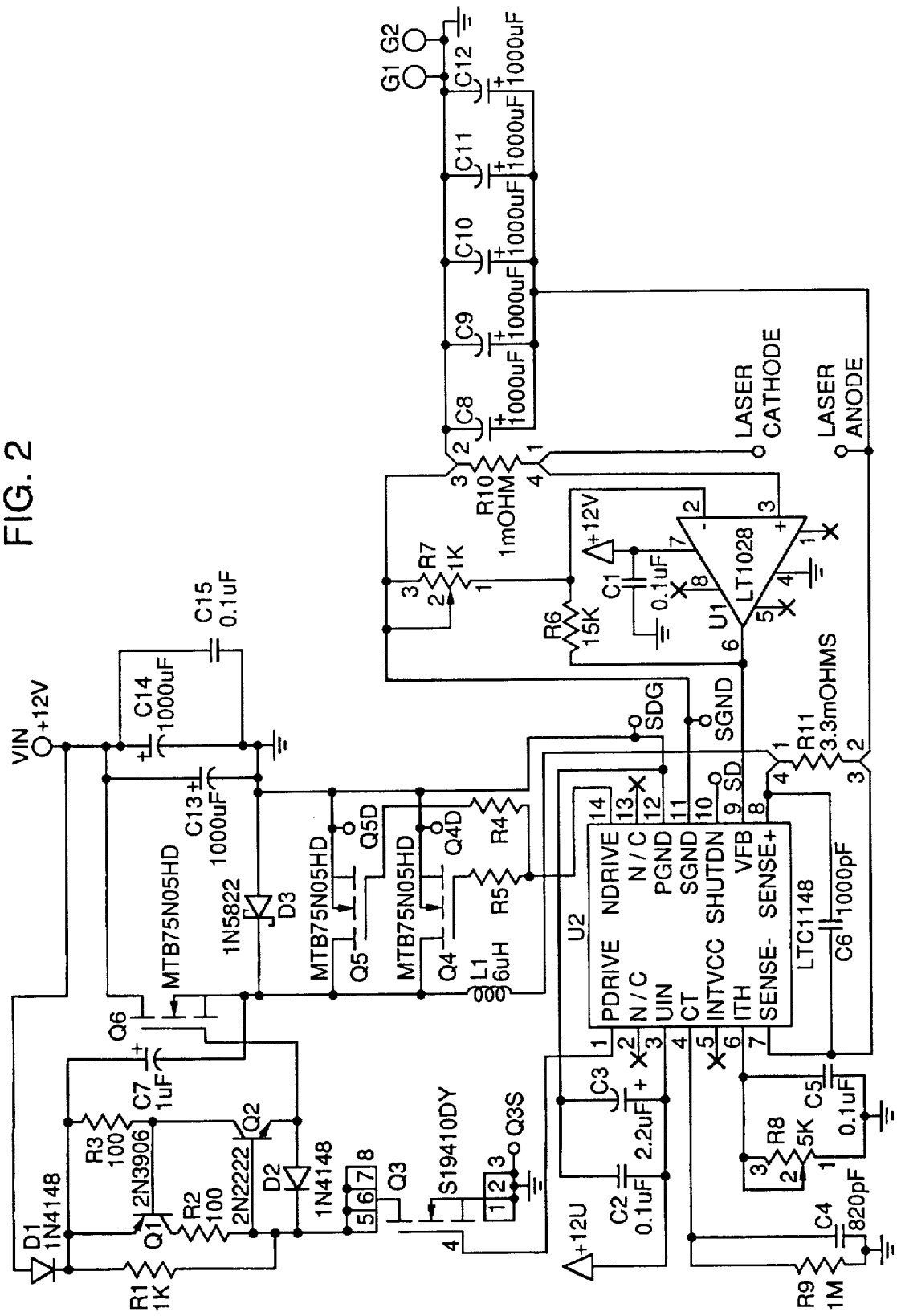
FIG. 2 is a circuit diagram of the system of FIG. 1.

In FIG. 1, the heart of the laser driver is a high efficiency constant voltage DC/DC switching power supply circuit 100 which has been modified and improved to provide the necessary highly controlled constant current which is needed for state-of-the-art laser diodes. The switching circuit 100 consists of an internal oscillator running at approximately 70 Khz, mosfet driving circuitry and voltage control sensing circuitry. The circuit alternately switches high and low side power mosfets which are connected to one end of a voltage transforming inductor as shown in FIG. 2. This produces a square wave at the input of the inductor which switches between the 12 volt input level and ground. The mosfets are very low on-resistance devices which typically have a resistance of 0.007 ohms, which greatly reduce the heat losses normally incurred when using transistors to switch power. The switching circuit also monitors the inductor current and prevents the output voltage from exceeding a preset level.

The current control for the circuit is provided by an additional section, the current sensing amplifier 110, which has been added to sense the current actually flowing through the laser device. To prevent heat losses, a 0.001 ohm current sensing resistor is used to provide a signal which is amplified and sent back to the switching controller unit. If the current in the laser 190 begins to rise, the feedback signal causes the switching controller 100 to modify the duty cycle to the power mosfets 150. This in turn brings the laser current back to the desired value. Using the method of current sensing and control, the laser current never varies more than a few milliamps when supplying up to 30 amps. The laser driver circuitry is able to keep the laser current constant down to an input voltage of 3.8 volts. This means that for a 12 volt battery power source, virtually all of the available power will be used from the battery before the laser current begins to drop, thus maximizing the possible run-time per battery charge.

Overall, the low loss, high efficiency, low current requirements for this laser driver circuit make it an unique solution for compact, light weight, battery operated laser devices to be used in the field.

The reader's attention is now directed towards FIG. 2, which is an electrical schematic of the laser driver circuit that performs the functions of the block diagram of FIG. 1. For example, the inductor L1 of FIG. 2 is the inductor 160 of FIG. 1. The values of all the electrical components are provided in FIG. 2, but these values may be modified for different applications.

The circuit has been used in the SABER 203, medpen, and medpacks field medical laser system to drive a laser diode. The circuit was able to supply the SABER 203 system 2.06 volts at 1.106 amps to a laser diode with a conversion efficiency of 90.93%. The input voltage was 6.52 volts.

In FIG. 2, the current sensing amplifier is made of R6, R7, R10, C1 and U1. The switching power supply consists of $U_2$ and all other components not included in the areas identified here. The power mosfets are Q4, Q5 and Q6.

Q6 and other components shown in the drawing comprise a bootstrap driver which allows a much lower resistance N-channel mosfet to be used instead of a P-channel mosfet which has an inherent higher "on" resistance and lower power handling capability.

Resistor $R_{10}$ is a current sensing resistor which monitors the current flowing through the laser. The voltage developed across $R_{10}$ is amplified by $U_1$, and its output is sent to pin 9 of U2. The voltage at this pin controls the duty cycle of the switching power supply. Because the voltage supplied to the laser is determined by the duty cycle, which is in turn controlled by the laser current flowing through $R_{10}$, the voltage to the laser is varied as needed to keep the laser current constant.

While the invention has been described in its presently preferred embodiment it is understood that the words which have been used are words of description rather than words of limitation and that changes within the purview of the appended claims may be made without departing from the scope and spirit of the invention in its broader aspects.

What is claimed is:

1. A constant current laser driver which provides a voltage output signal for a laser and which comprises:

a voltage source, which produces a standard voltage signal, wherein said voltage source comprises a direct current battery that produces said standard voltage signal at a voltage level selected between 6 and 12 volts;

a means for converting the standard voltage signal from said voltage source into said voltage output signal for said laser, a means for adjusting said converting means so that said voltage output signal is maintained for said laser with a high power and constant current as said laser experiences varying load conditions, said adjusting means electrically connecting said converting means with said laser to conduct said voltage output signal thereto, said adjusting means providing a feedback adjustment signal to said converting means to maintain constant current levels in said voltage output signal.

2. A constant current laser drives, as described in claim 1, wherein said converting means comprises:

a transformer driving circuit that produces a square wave input signal;

a voltage transforming inductor circuit that is driven by the square wave input signal of the transformer driving circuit, and which converts that standard voltage signal of the voltage source into the voltage output signal at a present voltage level for the laser and at a current level that is proportioned to the square wave input signal of the driving circuit; and a voltage control sensing circuit that adjusts the square wave input signal of the transformer driving circuit in response to the feedback adjustment signal of said adjusting means.

3. A constant current laser driver, as defined in claim 1, wherein said laser comprises a diode laser scalpel system, and wherein said converting means comprises a direct current-to-direct current transformer circuit that converts said standard voltage signal into said voltage output signal at about a 2 volt level and laser output power selected from a range of 1–20 watts and at electrical currents of up to 30 amps.

4. A constant current laser driver, as defined in claim 2, wherein said laser comprises a diode laser scalpel system, and wherein said voltage transforming inductor circuit comprises a direct current-to-direct current transformer circuit that converts said standard voltage signal into said voltage output signal at about a 2 volt level and laser output power selected from a range of 1–20 watts and at electrical currents of up to 30 amps.

* * * * *